(12) United States Patent
Sohn et al.

(10) Patent No.: US 7,279,883 B2
(45) Date of Patent: Oct. 9, 2007

(54) PARTICLE ANALYZER AND METHODS FOR USE THEREOF

(75) Inventors: Lydia L. Sohn, 5 Campbell Woods Way, Princeton, NJ (US) 08540; Omar A. Saleh, 226D Harrison La., Princeton, NJ (US) 08540

(73) Assignees: Lydia L. Sohn, Oakland, CA (US); Omar A. Saleh, Holmdel, NJ (US)

( * ) Notice: Subject to any disclaimer, the term of this patent is extended or adjusted under 35 U.S.C. 154(b) by 0 days.

(21) Appl. No.: 10/056,103

(22) Filed: Jan. 23, 2002

(65) Prior Publication Data

US 2002/0140414 A1 Oct. 3, 2002

Related U.S. Application Data

(60) Provisional application No. 60/263,470, filed on Jan. 23, 2001.

(51) Int. Cl.
*G01N 27/00* (2006.01)
(52) U.S. Cl. ....................................................... 324/71.4
(58) Field of Classification Search ................ 324/71.4
See application file for complete search history.

(56) References Cited

U.S. PATENT DOCUMENTS

| 3,919,050 | A | * | 11/1975 | Curby ........................ 435/39 |
| 3,944,917 | A | * | 3/1976 | Hogg et al. ................. 324/71.1 |
| 3,984,307 | A | | 10/1976 | Kamentsky et al. |
| 4,607,526 | A | * | 8/1986 | Bachenheimer et al. ... 324/71.4 |
| 4,810,650 | A | | 3/1989 | Kell et al. ................... 435/291 |
| 5,376,878 | A | * | 12/1994 | Fisher ........................ 324/71.4 |
| 5,744,366 | A | * | 4/1998 | Kricka et al. ................. 436/63 |
| 5,824,477 | A | | 10/1998 | Stanley ........................... 435/6 |
| 6,168,948 | B1 | * | 1/2001 | Anderson et al. ......... 435/287.2 |
| 6,426,615 | B1 | * | 7/2002 | Mehta ........................ 324/71.4 |

FOREIGN PATENT DOCUMENTS

| WO | WO94/02846 | 2/1994 |
| WO | WO 00/49385 | 8/2000 |
| WO | WO 01/18246 | 3/2001 |

OTHER PUBLICATIONS

Duffy et al., "Rapid Prototyping of Microfluidic Systems in Poly(dimethylsiloxane)", (1998) Analytical Chemistry, vol. 70, No. 23, pp. 4974-84.

DeBlois et al., "Counting and sizing of submicron particles by the resistive pulse technique", (1970) Rev. Sci. Instrum., Database accession No. 194870, XP002215413, Abstract.

(Continued)

*Primary Examiner*—Andrew H. Hirshfeld
*Assistant Examiner*—Timothy J Dole
(74) *Attorney, Agent, or Firm*—Townsend and Townsend and Crew LLP

(57) ABSTRACT

A quantitative microchip Coulter counter is provided for use in detecting and measuring particles or macromolecules. The device comprises a conduit, a fluid handling system, and a measurement system. Preferably, the conduit is at least in part formed from an elastomeric material.

27 Claims, 11 Drawing Sheets

OTHER PUBLICATIONS

Communication relating to the results of the partial international search, PCT/US02/02144, mailed Nov. 15, 2002, EPO.

Koutsouris et al., "Determination of Erthrocyte Transit Times Through Micropores", Biorheology, vol. 25, pp. 763-772, 1988.

Koch et al., "Two Simple Micromixers Based on Silicon", J. Micromech. Microeng., pp. 123-126, 1988.

Tracey et al., "A Silicon Micromachined Device for Use in Blood Cell Deformability Studies", IEEE Transactions on Biomedical Engineering, vol. 42, No. 8, pp. 751-761, Aug. 1995.

DeBlois et al., "Counting and Sizing of Submicron Particles by the Resistive Pulse Technique", The Review of Scientific Instruments, vol. 41, No. 7, pp. 909-916, Jul. 1970.

Koch et al., "Design and Fabrication of a Micromachined Coulter Counter", J. Micromech. Microeng., vol. 9, pp. 159-161, 1999.

DeBlois et al., "Electrokinetic Measurements with Submicron Particles and Pores by the Resistive Pulse Techniques", Journal of Colloid and Interface Science, vol. 61, No. 2, pp. 323-335, Sep. 1977.

Asami et al., "Real-Time Monitoring of Yeast Cell Division by Dielectric Spectroscopy", Biophysical Journal, vol. 76, pp. 3345-3348, Jun. 1999.

Chou et al., "A Microfabricated Device for Sizing and Sorting DNA Molecules", Proc. Natl. Acad. Sci. USA, vol. 96, pp. 11-13, Jan. 1999.

Saleh et al., "Quantitative Sensing of Nanoscale Colloids using a Microchip Coulter Counter", Review of Scientific Instruments, vol. 72, No. 12, pp. 4449-4451, Dec. 2001.

Saleh et al., "A Quantitative Nanoscale Coulter Counter", Abstract for presentation at Oct. 2001 MicroTAS conference, in Monterey, CA, 3 pages.

Saleh et al., "A Quantitative Nanoscale Coulter Counter" Presentation at Oct. 2001 MicroTAS conference, in Monterey, CA, 17 pages.

Unger et al., "Monolithic Microfabricated Valves and Pumps by Multilayer Soft Lithography", Science, vol. 288, pp. 113-116, Apr. 7, 2000.

Quake et al., "From Micro- to Nanofabrication with Soft Materials", Science, vol. 290, pp. 1536-1540, Nov. 24, 2000.

Fu et al., "A Microfabricated Fluorescence-Activated Cell Sorter", Nature Biotechnology, vol. 17, pp. 1109-1111, Nov. 1999.

Sun et al., "Fabrication and Characterization of Single Pores for Modeling Mass Transport across Porous Membranes", Langmuir, vol. 15, pp. 738-741, 1999.

Larsen et al., "Microchip Coulter Particle Counter", Transducers '97, pp. 1319-1322, 1997.

Fan et al., "Micromachining of Capillary Electrophoresis Injectors and Separators on Glass Chips and Evaluation of Flow at Capillary Intersections", Analytical Chemistry, vol. 66, No. 1, pp. 177-184, Jan. 1, 1994.

* cited by examiner

PARTICLE ANALYZER AND METHODS FOR USE THEREOF

RELATED APPLICATIONS

This application claims priority under 35 U.S.C. § 119(e) to U.S. Ser. No. 60/263,470, filed Jan. 23, 2001, which is incorporated by reference in their entirety for all purposes.

STATEMENT OF GOVERNMENT INTEREST

This invention was made with government support under DARPA Grant No. DAAD190010369 and NSF Grant No. DMR9624536. As such, the United States government has certain rights in this invention.

FIELD OF THE INVENTION

The present invention relates generally to the analysis of biological solutions. More particularly, it relates to the detection of particles ranging in size from sub-micron to several microns in solutions.

BACKGROUND OF THE INVENTION

Quantitative measurements of the size and concentration of macromolecules, such as proteins and DNA, is useful for many biological assays as well as studies of colloidal and macromolecular solutions. Traditionally, this has been accomplished through ultracentrifugation, chromatography, and especially, gel electrophoresis. See, Alberts et al. (1994) Molecular Biology of the Cell, Garland Publishing, Inc., NY.

Coulter counters typically consist of two fluid-filled reservoirs of particle-laden solution separated by a membrane and connected by a small aperture or pore in that membrane. Particles in the solution are driven through the pore and in doing so, displace conducting fluid and raise the electrical resistance of the pore. By monitoring the changes in electrical current through the pore as individual particles pass from one reservoir to the other, Coulter counters are able to measure the sizes of particles passing through the pore.

While this method has long been used to characterize solutions of micron- (or greater) size cells, its relative simplicity has led to efforts to employ it to detect sub-micron particles, including viruses. See, Kubitschak (1968) Nature 182:234; Gregg et al. (1965) Biophys. J. 5:393; DeBlois et al. (1970) Rev. Sci. Instrum. 41:909; and DeBlois et al. (1977) J. Colloid Interface Sci. 61:323.

Coulter conduits typically having diameters ranging between approximately 0.015 mm and 0.200 mm, with conduit length-to-diameter ratios L/D between 0.75 and 1.2, have proven useful for a great variety of particles. Resolutions down to particle sizes of 0.6 µm have been reported.

Sun and Crooks have proposed a method for fabricating single pores in a gold membrane. However, use of the gold membrane results in problematic charging effects, which reduce the time resolution of measurements. See, Sun et al. (1999) Langmuir 15:738. Moreover, their device utilizes a pore that runs from one side to the other side of the substrate.

Koch et al. (1999) J. Micromech. Microeng. 9:159 describes a device having a pore of ~5 micron diameter. The device is capped with a glass sheet which must be adhered to the substrate via high-temperature electrical bonding procedures. Moreover, the fluid access in the Koch device is from the backside of the chip.

Genetically-modified transmembrane protein pores, suspended in lipid bilayers and molecular-scaled holes in silicon nitride have also been used as engineered nanopores. However, these strategies suffer from difficulties in creating an effective and stable pore or array of pores. See, Howorka et al. (201) Nature Biotechnology 19:636.

Miniaturization of a Coulter counter would allow for other applications such as the characterization of biological cells, e.g., red blood cells, colloids, or even biological molecules. It is desirable that simple apparatus for sensing and characterizing particles be provided which offers increased sensitivity to particle characteristics.

SUMMARY OF THE INVENTION

The present invention provides a device that allows the Coulter principle to be applied to the detection and measurement of particles ranging in size from sub-micron to several microns. The device comprises a conduit through which a liquid suspension of particles to be sensed and characterized can be made to pass, wherein the conduit has an effective electrical impedance which is changed with the passage of each particle therethrough; a liquid handling-system for causing the liquid suspension of particles to pass through the conduit; and a measurement system for sensing the change of electrical impedance in the conduit In one embodiment, the conduit has a cross-sectional area of less than about 1 µm$^2$ and a length of less than about 10 µm. According to another embodiment, the conduit is formed at least in part by an elastomeric material. The conduit may have be of a variety of shapes and sizes, with either rectangular or circular cross-sections being particularly preferred.

In a preferred embodiment, a multi-point measurement system is used to sense the change in electrical impedance of the conduit. Preferably, a four-point electrode system is used.

The device may be integrated with other microfluidics or nanofluidics systems, including units for delivering the liquid suspension of particles to the liquid handling system; optical detection units; filtration systems; gating systems; particle sorters; dilution systems; and the like.

The device can be fabricated using microfabrication techniques. In one embodiment, the device comprises a substrate into which the reservoirs and conduit have been etched as channels. The device is completed by patterning electrodes in the reservoirs and sealing the channels with an elastomeric cap. In another embodiment, the substrate supports the electrodes. The conduit and the reservoirs are formed in the elastomeric cap. The device is completed by aligning the cap to the electrodes and sealing the cap to the substrate.

The invention also provides methods for sensing and characterizing particles by the Coulter principle. These methods require little sample preparation and thus, are preferred to optical detection techniques. According to such methods, a liquid suspension of particles to be sensed and characterized is passed through a conduit, as described above. The electrical current through the conduit, or the voltage required to maintain the current, is monitored so as to sense the approach of particles to, the presence and characteristics of particles passing through, or the departure of particles from, the conduit.

The present invention, in its preferred embodiments will now be discussed in detail, with reference to the figures listed below.

DETAILED DESCRIPTION OF PREFERRED EMBODIMENTS

The invention provides a device that can sense submicron particles in solution in a manner similar to a Coulter counter. More specifically, the present device can detect and measure objects of macromolecular size (e.g., less than 1 µm). The device is fabricated using conventional microfabrication techniques. Such techniques allow for the precise control of the conduit dimensions which can be easily confirmed using optical and atomic force microscopy. Knowing the exact conduit dimensions allows for the quantitative prediction of the response of the device to particles of various sizes. Devices with conduits having lateral dimensions between 400 nm and 1 µm have been fabricated and used to detect and measure latex colloidal particles as small as 87 nm in diameter. The ability of the device to detect and measure ~500 nm diameter colloids with a resolution of ±10 nm has been demonstrated.

Generally, the device comprises a conduit through which a liquid suspension of particles can be made to pass. The conduit has an effective electrical impedance which is temporarily or permanently changed with the passage of each particle through. The device further comprises a liquid handling-system for causing the liquid suspension of particles to pass through the conduit and a measurement system for sensing the change of electrical impedance in the conduit.

Figure 1A:
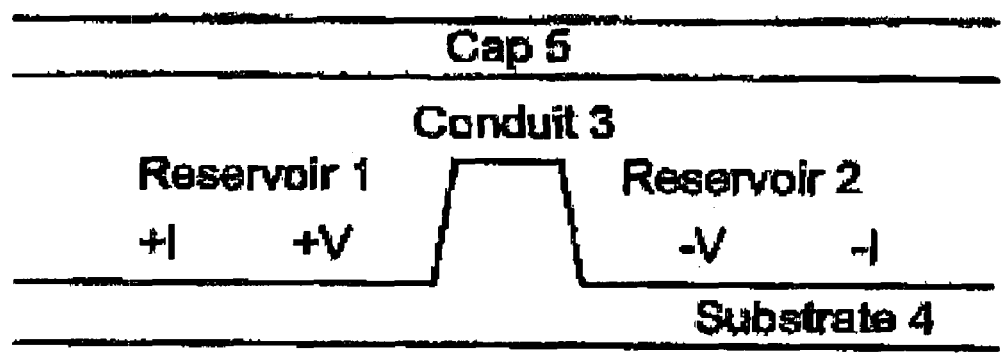
FIGS. 1A and B are schematic top and side views of a microchip Coulter counter of the invention.
Figure 1B:
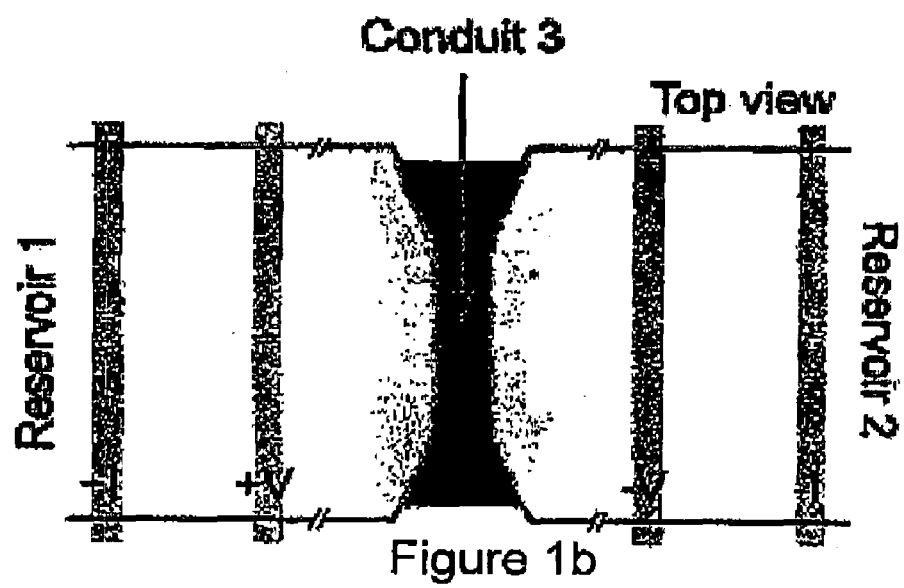
Figure 2A:
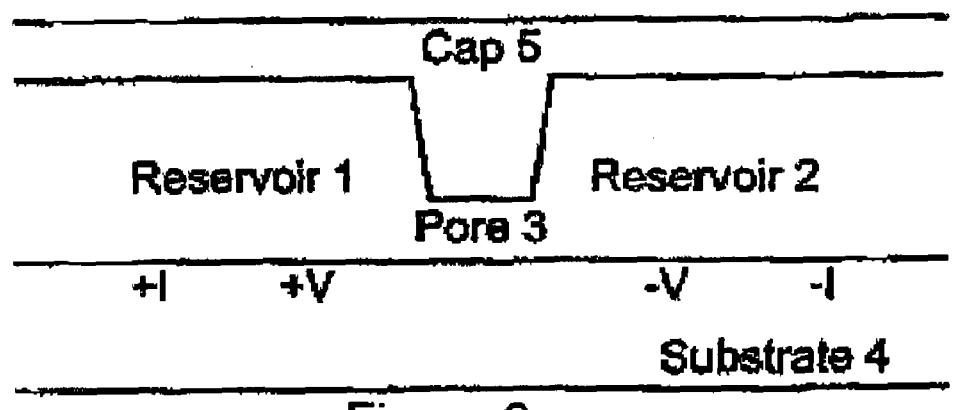
FIGS. 2A and B are schematic top and side views of a microchip Coulter counter of the invention. An optical image of an actual conduit sealed to a glass coverslip is incorporated into the top view.
Figure 2B:
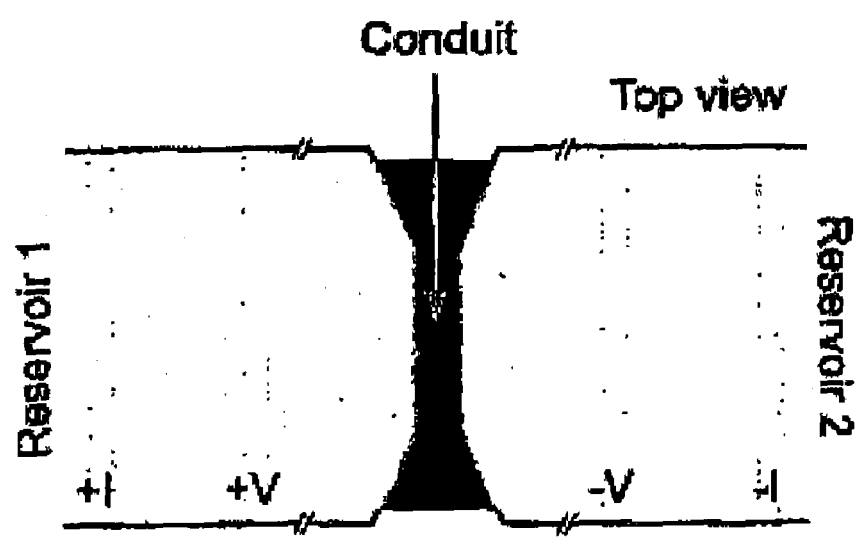

In FIG. 1 and FIG. 2 are schematically illustrated, in accordance with a preferred embodiment of the invention, a device for sensing and characterizing particles. The device of the invention comprises two reservoirs, 1 and 2, separated by conduit 3, on top of a substrate 4. The devices depicted in FIG. 1 and FIG. 2 differ in the method by which the conduit is formed. More specifically, in the device shown in FIG. 1, conduit 3 is etched into substrate 4 which is then sealed by an elastomeric cap 5. In the device shown in FIG. 2, the conduit 3 and reservoirs are formed in the elastomeric cap 5 which is than laid on top of substrate 4. For ease in manufacture and use, each of the components of the device are located on the same side of the substrate.

The Substrate

Suitable substrate materials are generally selected based upon their compatibility with the conditions present in the particular operation to be performed by the device. Such conditions can include extremes of pH, temperature, ionic concentration, solvent tolerance and application of electric fields. Additionally, substrate materials are also selected for their inertness to critical components of an analysis to be carried out by the system. Useful substrate materials include, e.g., glass, quartz, ceramics, and silicon, as well as polymeric substances, e.g., plastics. Although quartz or glass is preferably used as the substrate, in other embodiments silicon or another inert material of similar physical qualities can be used.

In a preferred embodiment, substrate 4 comprises a material, usually electrically insulating, with a low dielectric constant. Preferably, the substrate will have a dielectric constant of less than about 10. A low dielectric constant is desirable to decrease parasitic capacitance, and thereby increase the achievable time resolution. In the case of conductive or semiconductive substrates, there should be an insulating layer on the substrate. This is important for two reasons. Firstly, since the measurement itself may be compromised by a readily conducting substrate, and secondly since the system may use electrophoretic, electroosmotic, and/or electrokinetic forces to move materials about the system.

In the case of polymeric substrates, the substrate materials may be rigid, semi-rigid, or non-rigid, opaque, semi-opaque, or transparent, depending upon the use for which they are intended. For example, systems which include an optical or visual detection element are generally fabricated, at least in part, from optically transparent materials to allow, or at least, facilitate that detection. Alternatively, optically transparent windows of glass or quartz, e.g., may be incorporated into the device for these types of detection. Optically transparent means that the material allows light of wavelengths ranging from 180 to 1500 nm, usually from 220 to 800 nm, more usually from 250 to 800 nm, to have low transmission losses. Such light transmissive polymeric materials will be characterized by low crystallinity and include polycarbonate, polyethylene terepthalate, polystyrene, polymethylpentene, fluorocarbon copolymers, polyacrylates (including polymethacrylates, and more particularly polymethylmethacrylate (PMMA)), and the like.

Additionally, the polymeric materials may have linear or branched backbones, and may be crosslinked or non-crosslinked. Examples of particularly preferred polymeric materials include, e.g., polydimethylsiloxanes (PDMS), polyurethane, polyvinylchloride (PVC), polystyrene, polysulfone, polycarbonate, polymethylmethacrylate (PMMA) and the like.

Substrate 4 may additionally be provided with access ports and/or reservoirs for introducing the various fluid elements needed for a particular analysis.

In a preferred embodiment, planar substrate 4 comprises a transparent material such as quartz or glass, allowing optical interrogation of the conduit and/or reservoirs.

The Cap

Besides the substrate, the device includes an element which overlays the substrate to enclose and fluidly seal the various channels to form the conduit and reservoirs. Cap 5 may additionally be provided with access ports and/or reservoirs for introducing the various fluid elements needed for a particular analysis as well as outlets for eliminating the various fluids.

Cap 5 may be attached to the substrate by a variety of means, including, e.g., thermal bonding, adhesives, or in the case of certain substrate, e.g., quartz, glass, or polymeric substrates, a natural adhesion between the two components. Preferably, cap 5 comprises an elastomeric material as the elastomeric cap will form a reversible hermetic seal with nearly any smooth planar substrate. An advantage to forming a seal this way is that the elastomeric cap may be peeled up, washed, and re-used. Alternatively, the elastomeric cap may be bonded onto a flat elastomer, quartz, or glass layer, forming a permanent and high-strength bond. This may prove advantageous when higher back pressures are used. See, also Quake et al. (2000) Science 290:1536-1540, which is incorporated herein by reference.

Bonding methods may be used to secure the cap to the substrate, including activating the elastomer surface, for example by plasma exposure, so that the elastomeric cap/substrate will bond when placed in contact. See, e.g., Duffy et al, "Rapid Prototyping of Microfluidic Systems in Poly (dimethylsiloxane)", Analytical Chemistry (1998), 70, 4974-4984, and PCT WO 01/18246, each of which is incorporated herein by reference. Preferably, both cap 5 and substrate 4 are oxidized in a (DC- or AC-generated) oxygen plasma to insure the hydrophilicity of the reservoir and conduit and to strengthen the seal to the quartz substrate.

Cap 5 may be fabricated from a wide variety of elastomers. Common elastomeric polymers include polyisoprene, polybutadiene, polychloroprene, polyisobutylene, poly(styrene-butadiene-styrene), the polyurethanes, and silicones. In addition, polymers incorporating materials such as chlorosilanes or methyl-, ethyl-, and phenylsilanes, and polydimethylsiloxane (PDMS) such as Dow Chemical Corp. Sylgard 182, 184 or 186, or aliphatic urethane diacrylates such as (but not limited to) Ebecryl 270 or Irr 245 from UCB Chemical may also be used. See, e.g., Allcock et al, Contemporary Polymer Chemistry, 2nd Ed., which is incorporated herein by reference.

The following is a non-exclusive list of materials which may be utilized in connection with the present invention: polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride—hexafluoropropylene) copolymer (Viton), and elastomeric compositions of polyvinylchloride (PVC), polysulfone, polycarbonate, polymethylmethacrylate(PMMA), and polytertrafluoroethylene (Teflon).

Besides the substrate, the device optionally includes an additional planar cover element (not shown) which overlays cap 5, i.e, cap 5 is applied to the bottom surface of the cover element and thus, forms an interface between the cover element and the substrate. This planar cover element may be attached to cap 5 by a variety of the means, including, e.g., thermal bonding, adhesives or, in the case of glass, or semi-rigid and non-rigid polymeric substrates, a natural adhesion between the two components. The planar cover element may additionally be provided with access ports and/or reservoirs for introducing the various fluid elements needed for a particular screen.

In an exemplary aspect, cap 5 is fabricated from polydimethylsiloxane (PDMS) or comprises a PDMS coated glass coverslip. However, the present systems are not limited to this one formulation, type or even this family of polymer; rather, nearly any elastomeric polymer is suitable.

The Reservoirs

Applying the cap 5 to the substrate 4 results in the formation of two or more enclosed reservoirs (1 and 2) connected by a conduit 3. Each of the reservoirs 1 and 2 is adapted to contain a liquid medium M which comprises a liquid suspension of particles. Preferably, the reservoirs will have a depth of less than about 10 μm, and more preferably, about 5 μm.

Figure 6:
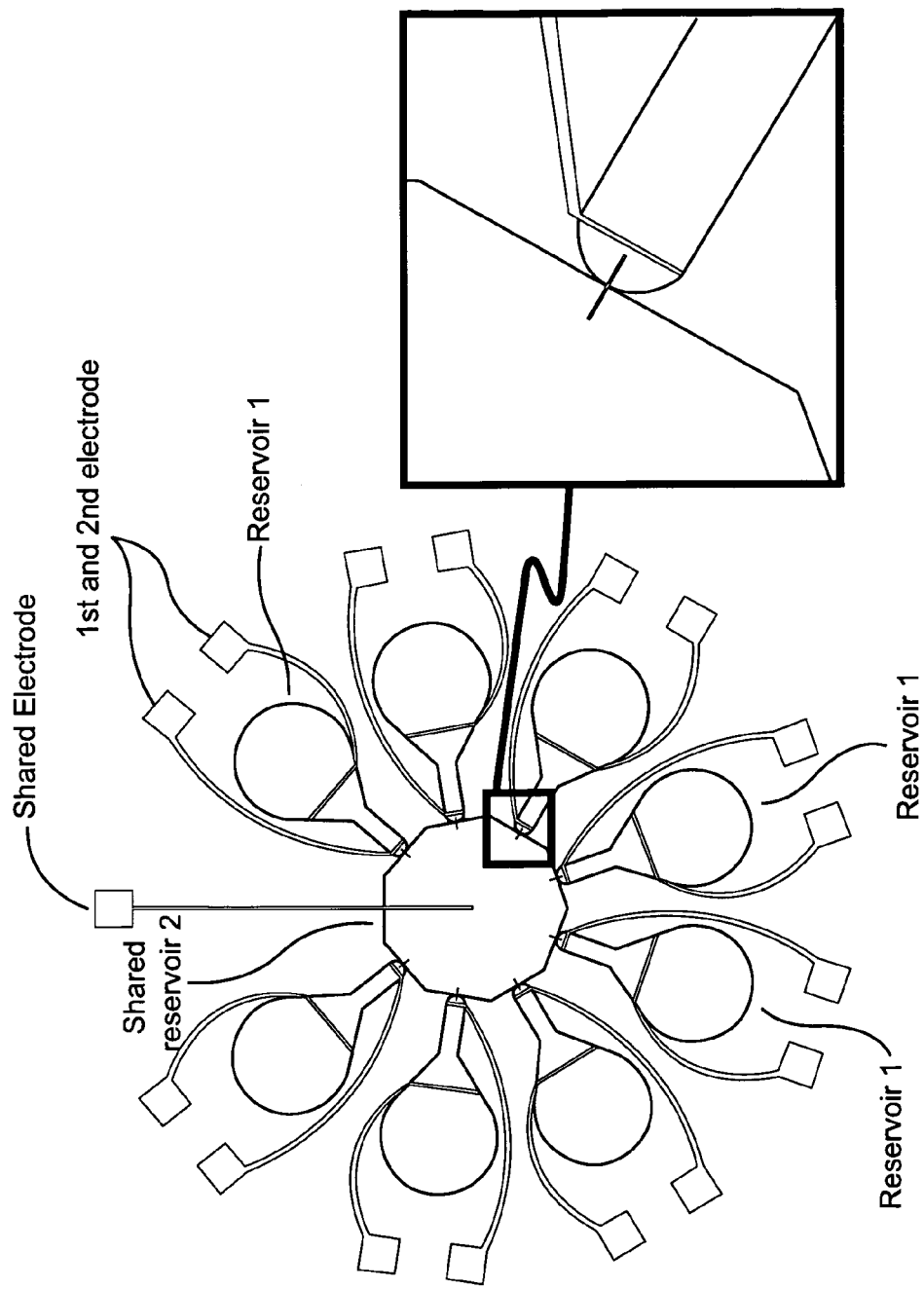
FIG. 6 is a schematic diagram of an eight-conduit Coulter counter of the invention.

Use of a multi-point measurement system allows considerable flexibility in the reservoir design. As such, a wide range of reservoir depths and widths can be used, as permitted by the material and technique used in fabrication. Moreover, as shown in FIG. 6, each of the reservoirs do not have to be the same size or shape.

Liquid medium M is introduced into the reservoirs through an inlet or access port. Likewise, liquid medium can be transferred from the reservoirs through an outlet port. A wide range of suitable sizes of inlets and outlets are possible, and those of skill in the art are capable of empirically determining the preferred size ranges depending upon the nature of the liquid or the particles to be analyzed. The size of the inlet or the outlet is not a limiting factor.

In operation, the reservoirs are filled by capillary action: a drop of solution placed at the edge of the substrate or within the access port is immediately drawn into the reservoirs. Alternatively, the reservoirs can be filled by driving the solution into it using an applied pressure such as can be produced using a pump, such as a syringe pump. Other means for enabling the fluid to move through the device also can be used, for example, but not by way of limitation, devices that force fluid into the device using electric fields. In some cases, it is possible to incorporate a filter into the reservoir so as to keep overly large particles from clogging the conduit.

The Conduit

As described in more detail below, the conduit 3 can be formed by a variety of methods. More specifically, according to one embodiment, conduit 3 is etched into substrate 4 which is then sealed by elastomeric cap 5. See, FIG. 1. Alternatively, as shown in FIG. 2, conduit 3 can be molded into elastomeric cap 5 which is then laid on top of substrate 4.

The dimensions of conduit 3 will vary with the size and shape of the particles to be measured. The cross sectional area of the conduit may be circular, square or rectangular, with square being particularly preferred. However, for some applications, it may be desired to use other conduit shapes. For example, for particles having a large aspect ratio, it may be desirable to use a rectangular conduit so that the particles may only transit through the conduit in a limited number of conformations.

Generally, conduit 3 will have a diameter of from about 0.1 to about 1 µm. Preferably, the conduit will have a cross section of about 1 µm$^2$. The length of the conduit will generally be greater than its diameter and will be from about 0.1 and about 50 micrometers, and preferably from about 1 to about 10 µm. Preferably, the ratio of the length of the conduit to the diameter will be about 10:1. Preferably, the volume ratio (i.e., the ratio of the volume of the particle to the volume of the conduit) will be from about 0.0001 to about 0.5; more preferably, from about 0.001 to about 0.2, and most preferably, from about 0.01 to about 0.1.

The Measurement System

Generally, a measurement system comprises any means for measuring the change of effective electrical impedance of the conduit with the passage of each particle therethrough. As one of skill in the art will appreciate, a variety of mechanisms are available for measuring impedance, including, but not limited to two-point (i.e., two-electrode), three-point, and four-point measurement systems.

Preferably, the measurement system is capable of quantification of uncompensated electrical resistance (extraneous resistance that is in series with the conduit resistance) arising from the fluid leading to the conduit. Thus, in a preferred embodiment, the measurement system comprises a four-point measurement system having two inner electrodes and two outer electrodes (i.e., a four-point measurement system) as shown in FIG. 1 or FIG. 2. In one mode, the outer electrodes pass a constant current, and the inner electrodes are used to measure changes in voltage; in another mode, the inner electrodes hold a constant voltage, while the outer electrodes are used to measure changes in current. Preferably, the outer electrodes inject current into the solution whereas the inner electrodes control the voltage applied to the conduit, but pass no current.

In multiple conduit systems, it may be desirable to use a three-point measurement system. Each of the units would have an unique set of electrodes (i.e., two individual electrodes) and all of the units would share a common third electrode.

The electrodes generally will be fashioned on the substrate. For example, the electrodes can be made by depositing metal onto the surface of the substrate. The electrodes (and their respective interconnectors to signal generation means and signal detection means) can comprise any biocompatible substance such as gold, silver, titanium, copper, platinum, iridium, polysilicon, carbon or aluminum. Preferably, the electrodes comprise titanium and platinum or titanium and silver.

Typically, the electrodes are configured so as to be symmetric and equidistant from the conduit. However, this is not strictly necessary. Indeed, it may be desirable to fashion an excess number of electrodes onto the substrate. More specifically, when using the cast cap, an excess number of electrodes, e.g., 10 or more or even 12 or more, may be applied to the surface of the substrate. The electrodes are applied in a pattern such that when the cap is applied onto the surface of the substrate, the desired measurement system is formed. Use of an excess number of electrodes, thus, decreases issues associated with aligning the cast cap on the substrate.

The inner electrodes optimally are situated close to the conduit. In a preferred embodiment having 4×200 µm$^2$ reservoirs, the inner electrodes are about 40 µm from the conduit. However, when uncompensated resistance arising from the fluid in the reservoir is small (for example, when the reservoirs are very wide and deep compared to the conduit), the placement of the inner electrodes is very flexible. For example, in some circumstances, the inner electrodes can be placed up to about 1 mm from the conduit.

The measurement system can be configured so as to measure change in impedance, resistance or current. A particle's residence time in the conduit can be measured simultaneously with the measurement of the change in current. Moreover, it may be desirable to monitor the effects of voltage on the current. For example, different voltages could be applied and it would then be determined if the change in current scales linearly with the voltage. This state of some particles might change with applied electric field. As the electric field will vary with voltage, varying the voltage will provide information about the state of the particles. Such information could relate to conformational changes of a large, flexible molecule; changes of the effective charge of a particle due to the applied field affecting the counterion layer around the particle; and the like. In addition, a particle with a dipole moment would become more stringently aligned to a large electric field, which would change the range of peak sizes measured for the particle.

The measurement system may utilize either AC or DC current. For the former, the phase as well as the current could be measured. Typically, frequencies of up to at least 40 khz would be scanned. This technique can be useful in differentiating between particles based on charge.

Surface Modification

It may be desirable to modify the surface of the device to reduce or enhance the various driving forces (e.g., electroosmotic, electrokinetic, electrophoretic, and the like) through the conduit or the reservoirs, to reduce or enhance analyte adsorption to the walls of the conduit or the reservoirs, and the like. More specifically, the surface of the conduit can be functionalized; the surface of the reservoirs can be functionalized; or the surfaces of both can be functionalized. In the latter case, the surface of the reservoirs can be modified in the same manner or in a different manner from the functionalization of the conduit. The use of different surface modifications for the conduit and the reservoirs may serve to increase the sensitivity of the device to particular species of interest.

More specifically, the device can be readily modified by reducing or enhancing analyte adsorption to the walls of the reservoir to allow for the probing of many different molecular interactions. Methods of silane surface chemistry developed in the past twenty years can be applied to the substrate or the conduit, allowing hundreds of different molecules to be grafted onto the device's surface. The surface can be modified with a coating by using thin-film technology based, for example, on physical vapor deposition, thermal processing, or plasma-enhanced chemical vapor deposition. Alternatively, plasma exposure can be used to directly activate or alter the surface and create a coating. For instance, plasma etch procedures can be used to oxidize a polymeric surface (i.e., a polystyrene or polyethylene to expose polar functionalities such as hydroxyls, carboxylic acids, aldehydes, or other reactive moieties).

The coating may comprise an organic thinfilm. Methods for the formation of organic thinfilms include in situ growth from the surface, deposition by physisorption, spin-coating, chemisorption, self-assembly and plasma-initiated polymerization from gas phase. For example, a material such as dextran can serve as a suitable organic thinfilm. Other thinfilms include lipid bilayers; monolayers of polyarginine or polylysine; self-assembled monolayer; and the like. The coating may cover the whole surface of the device or only parts of it, e.g., the conduit or the reservoirs. A variety of techniques for generating patterns of coatings on the surface of a support are well known in the art and include, without limitation, microfluidics printing, microstamping, and microcontact printing.

Additional references describing methods for surface modification include U.S. Pat. No. 4,680,201; U.S. Pat. No. 5,433,898; U.S. Pat. No. 6,056,860; EP 665,430, EP 452, 055; and Encyclopedia of Polymer Science and Engineering "Adhesion and Bonding", Vol. 1, pp. 476 et seq (Wiley Interscience, 1985), each of which is incorporated herein by reference.

Representative Devices

Figure 3:
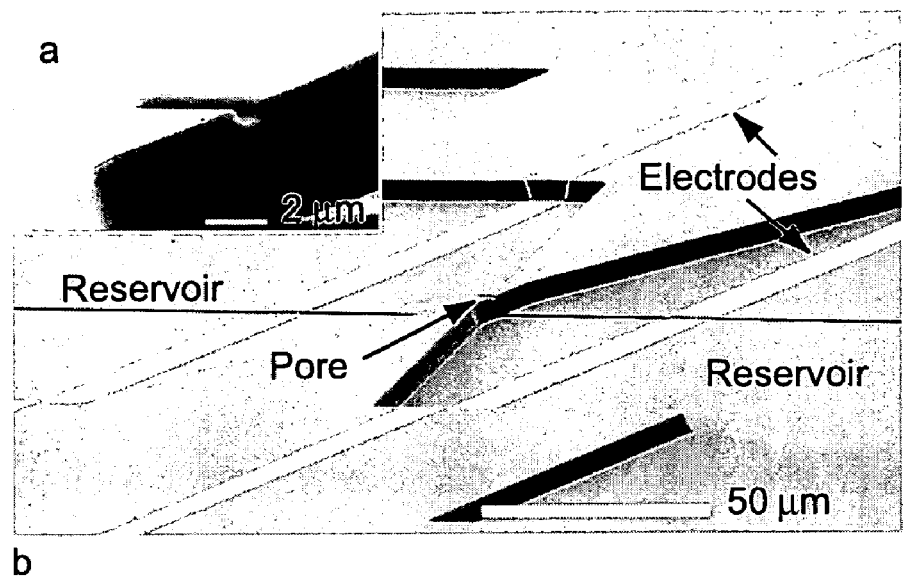
FIG. 3 is a scanning electron micrograph of a representative microchip Coulter counter. The device is shown without its cap. The reservoirs and inner electrodes are only partially shown. The outer electrodes are not visible.

A scanning electron micrograph of a representative device is shown in FIG. 3. The device was prepared by etching the conduit and reservoirs into a quartz substrate. The cap comprises a PDMS-lined glass coverslip. The device has 3.5 µm deep reservoirs. The device utilizes a four-point measurement system. The inner electrodes comprise Ti/Pt. The outer electrodes are not visible. FIG. 3 also shows a magnified view of the conduit which has dimensions 5.1×1.5×1. µm$^3$.

Figure 5:
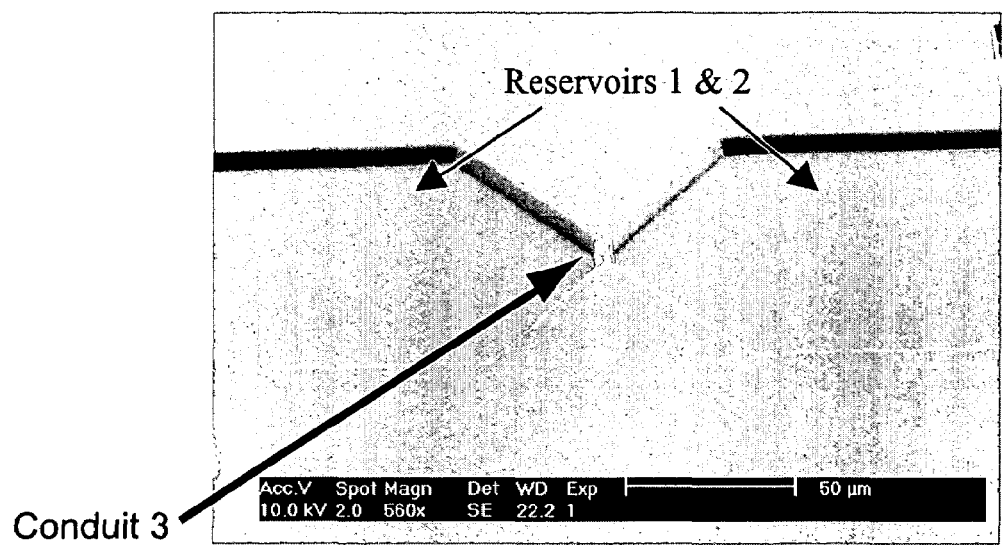
FIG. 5 is a SEM image of a microchip Coulter counter of the invention. The device is shown without its cap

A field emission scanning electron micrograph of another representative device is shown in FIG. 5. The device was prepared by molding the conduit and reservoirs into a PDMS cap. The device has a conduit of length 3 µm and 200 nm which connects the two 5 µm deep reservoirs. The substrate is a glass coverslip.

An eight-unit device is shown in FIG. 6. The device uses a three-point measurement system wherein each unit has unique electrodes and the third electrode is shared between the units. It should also be noted that the device is configured such that each of the units share a common reservoir as well as having a reservoir dedicated to such unit. This configuration, i.e., shared electrodes and/or shared reservoirs is preferentially used in multi-unit devices. Such multi-unit devices will generally comprise a plurality of conduits with the appropriate number of reservoirs, electrodes, etc to permit the sensing and characterizing of particles as they pass through the various conduits.

Methods of Fabricating the Present Invention

Manufacturing of devices may be carried out by any number of microfabrication techniques that are well known in the art. For example, lithographic techniques may be employed in fabricating glass, quartz or silicon substrates, for example, with methods well known in the semiconductor manufacturing industries. Photolithographic masking, plasma or wet etching and other semiconductor processing technologies define microscale elements in and on substrate surfaces. Alternatively, micromachining methods, such as laser drilling, micromilling and the like, may be employed. Similarly, for polymeric substrates, well known manufacturing techniques may also be used. These techniques include injection molding techniques or stamp molding methods where large numbers of substrates may be produced using, e.g., rolling stamps to produce large sheets of microscale substrates, or polymer microcasting techniques where the substrate is polymerized within a microfabricated mold.

Two exemplary methods of fabricating the present invention are provided herein. It is to be understood that the present invention is not limited to fabrication by one or the other of these methods. Rather, other suitable methods of fabricating the present devices, including modifying the present methods, are also contemplated.

As will be explained, one method involves a series of lithographic processes in which the reservoirs and conduit are etched into planar substrate 4. These methods can easily be used to make a large number of devices on a single chip, thus increasing efficiency through parallelization. This is in comparison to other proposals for the fabrication of small Coulter counters, which rely on difficult and inconsistent techniques that are suitable only in research situations. Conversely, the second method involves the fashioning of conduit 3 and reservoirs in elastomeric cap 5 which is then contacted with substrate 4.

The First Exemplary Method

Figure 11:
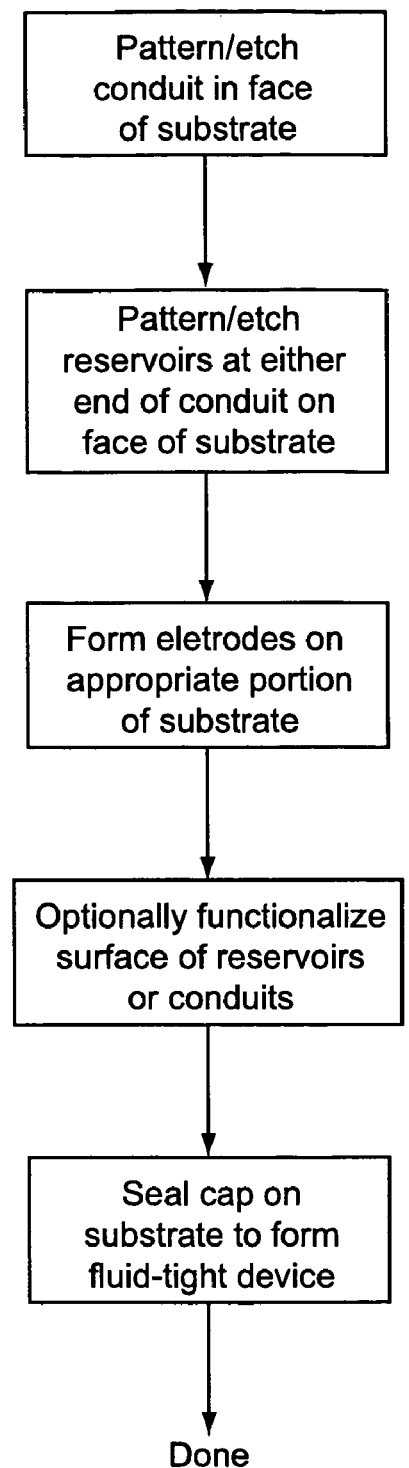
FIG. 11 shows a schematic diagram of the first exemplary method of fabricating a microchip Coulter counter as described herein.

According to the first exemplary method which is shown schematically in FIG. 11, two reservoirs connected by the conduit are photolithographically (PL) patterned and then etched into the quartz using a CHF$_3$ reactive ion etch (RIE). Electrodes are made by depositing metal in an electron beam evaporator (either titanium and platinum or titanium and silver) on another photolithographic pattern. Finally, substrate 4 is sealed on top with elastomeric cap 5 (preferably, a cover slip coated with an elastomer such as oxidized polydimethylsiloxane (silicone)). Each device can be used repeatedly by removing the seal, cleaning, then resealing with a new cap. Note that many different metals can be used for the electrodes, and that the size of the conduit can be greatly decreased by using electron beam lithography (EBL) to initially pattern the substrate.

Preferably, the device is fabricated in multiple stages, with each stage consisting of patterning with photolithography, followed by transferring the pattern onto a substrate using either reactive ion etching (RIE) or metal deposition and lift-off. The first stage is the fabrication of the channel which subsequently becomes the conduit. A line is patterned on the substrate using either photolithography for linewidths≧1 µm, or electron-beam lithography for linewidths between 50 and 500 nm, and then etched to a using a CHF$_3$ RIE.

The substrate is cleaned, and then undergoes a second stage of photolithography and RIE to define two reservoirs, preferably, each being 400 µm wide and 3.5 µm deep, separated by ~3-10 µm and connected by the previously-defined channel. The length of the conduit is defined in this second stage by the separation between the two reservoirs.

The final stage consists of the lithographic patterning of the electrodes, preferably four electrodes, in the reservoirs, followed by the deposition of 50/250Angstrom Ti/Pt in an electron beam evaporator, and ending with a lift-off of the excess metal. The metal deposition is carried out twice in succession with the sample position ±45° from normal to the flux of metal to ensure that the electrodes are continuous down both walls of the reservoirs. FIG. 3 shows a scanning electron micrograph of a completed device.

Cap 5, preferably, an elastomer-coated glass coverslip, is placed atop the substrate before each measurement. After each measurement cap 5 is removed and discarded, and the substrate is cleaned by chemical and ultrasonic methods. Thus, each device can be reused many times.

The Second Exemplary Method

Figure 12:
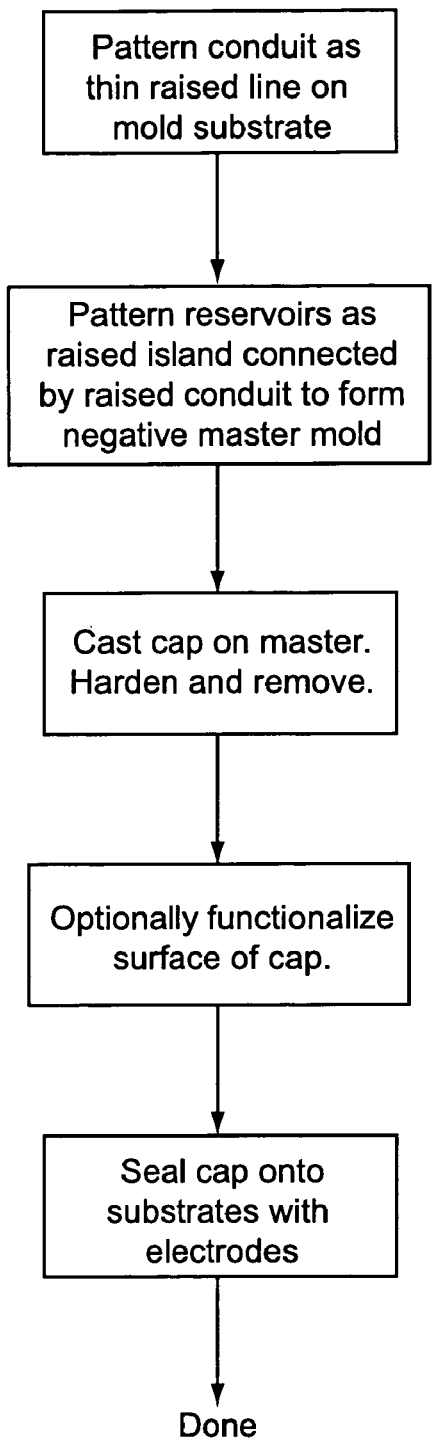
FIG. 12 shows a schematic diagram of the second exemplary method of fabricating a microchip Coulter counter as described herein.

According to the second exemplary method, as depicted in FIG. 12, conduit 3 and the reservoirs are molded into elastomeric cap 5. Preferably, a negative master mold is prepared from a suitable rigid substrate. The master can be used to cast one or preferably, multiple, copies of cap 5. The cap is then contacted with substrate 4 that further comprises two or more electrodes to form the microchip Coulter counter. See also, Chou et al. (1999) Proc. Natl. Acad. Sci. USA 96:11-13 and Xia et al. (1996) Micromolding of Polymers in Capillaries, Applications in Microfabrication. Chem. Mater. 8:1558-1567, each of which is incorporated herein by reference.

Referring to FIG. 12, the conduit is first patterned as a thin raised line on a rigid substrate, such as silicon or quartz. The reservoirs are then patterned onto the substrate as raised islands which are connected by the raised conduit to yield the master mold. The patterning steps may be accomplished by a number of conventional silicon processing methods, including but not limited to photolithography, ion-milling, and electron beam lithography.

More specifically, photolithography preferably is used to produce masters for devices having conduits with a diameter of about 1 μm or more. Silicon or quartz will be generally be used as the substrate and patterning will be conducted as known in the art.

Electron beam lithography (EBL) with a polystyrene spin-on process is typically used to fashion masters for devices with smaller conduits (e.g., having height and width adjustable from about 450 nm to less than 100 nm). The reservoirs can then be produced using conventional photolithography, preferably using a physically and chemically robust photoresist such as SU-8. Reservoirs having a 5 μm depth can be readily prepared using this technique. As one of skill in the art will appreciate, the conduit will need to be protected, e.g., through use of an etch mask, during generation of the reservoirs. See, also, Schmid and Michel (2000) Macromolecules 33, which is incorporated herein by reference.

An elastomeric layer is cast on top of the master mold such that two deeper recesses will be formed for the reservoirs and a narrow recess will be formed for the conduit in the bottom surface of elastomeric layer. More specifically, the recesses will correspond in dimension to the protrusions that were patterned previously. The cast material is allowed to harden and is removed from the master mold which can then be used for additional castings. The cap 5 is then laid atop substrate 4 with a plurality of electrodes thereon.

The elastomeric layer may be cast thick for mechanical stability. In an exemplary embodiment, the elastomeric layer is between about 1 mm and about 5 mm thick, and more preferably approximately about 3 mm thick. A non-exclusive list of ranges of thickness of the elastomer layer in accordance with other embodiments of the present invention is between about 0.1 micron to 10 cm, 1 micron to 5 cm, 10 microns to 2 cm, 100 microns to 10 mm.

Methods of Operating the Present Invention

Particles to be sensed and characterized are suspended at an appropriate concentration in a suitable liquid medium, e.g., liquid medium M. Liquid medium M generally will have an electrical impedance per unit volume that differs from that of the particles to be characterized. In general any liquid media (either aqueous or nonaqueous) comprising ionic species may be useful in specific applications of the new apparatus. Thus, many of the liquid media (e.g., isotonic saline) used with Coulter apparatus will find direct application. Liquid medium M is exemplified, but not limited to, liquids, such as water, organic solvents, cell cultures, animal or human bodily fluids, solutions comprising particles and/or biological molecules, cellular cytoplasm, cellular extracts, cellular suspensions, solutions of labeled particles or biological molecules, solutions comprising liposomes, encapsulated material, or micelles, etc.

Liquid medium M will further comprise the particles to be measured, which can include live cells, parts of cells such as ribosomes or nuclei, and/or macromolecules such as proteins or nucleic acids. Particles are defined as any small amount of material capable of causing a change in electrical characteristic of the conduit when the medium comprising the particles flows through the conduit. By way of example, but not by way of limitation, particles are any polymer particle, such as polystyrene beads, metal colloids, magnetic particles, dieletric particles, nanocrystals of material, bioparticles such as pores, pollen, cellular occlusions, precipitates, intracellular crystals, and biological molecules, including polynucleotides, such as DNA and RNA, polysaccharides, polypeptides, proteins, lipids, peptidoglycans, and any other cellular components.

The particles may be positively and/or negatively charged or even neutral. As such, a variety of driving mechanisms may be required to deliver the sample to the device. For example, electrophoretic, electrokinetic or electroosmotic forces, or pressure gradients could be used. The rate of flow in delivering the sample to the device, as well as the concentration of the medium, is selected to allow sufficient time for the device to detect and/or measure the electrical characteristic(s) of the particle to be measured.

Figure 4:
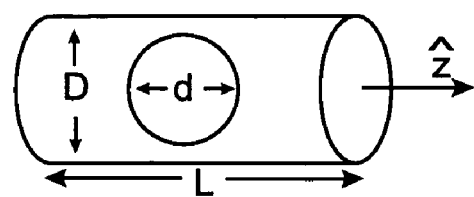
FIG. 4 is a schematic diagram of a spherical particle of diameter d in a conduit of diameter D and length L.

The sensitivity of a Coulter counter relies upon the relative sizes of the conduit and the particle to be measured. The resistance of a conduit $R_p$ increases by $\delta R_p$ when a particle enters since the particle displaces conducting fluid. $\delta R_p$ can be estimated for a conduit aligned along the z-axis by (see FIG. 4):

$$\delta R_p = \rho \int dx/A(x) - R_p \quad \text{(Equation 1)}$$

where A(z) represents the successive cross sections of the conduit containing a particle. See, Gregg and Steidley supra. For a spherical particle of diameter d in a conduit of diameter D and length L, the relative change in resistance is $$\frac{\delta R_p}{R_p} = \frac{D}{L}\left[\frac{\arcsin(d/D)}{(1-(d/D)^2)^{1/2}} - \frac{d}{D}\right] \quad \text{(Equation 2)}$$

Equations 1 and 2 assume that the current density is uniform across the conduit, and thus is not applicable for cases where the cross section A(z) varies quickly, i.e., where d<<D. For this particular case, Deblois and Bean formulated an equation for $\delta R_p$ based on a solution of the Laplace equation:

$$\frac{\delta R_p}{R_p} = \frac{d^3}{LD^2}\left[\frac{D^2}{2L^2} + \frac{1}{\sqrt{1+(D/L)^2}}\right] F\left(\frac{d^3}{D^3}\right) \quad \text{(Equation 3)}$$

where $F(d^3/D^3)$ is a numerical factor that accounts for the bulging of the current streamlines around the sphere. When employing Equation 3 to predict resistance changes, an effective value for D is found by equating the cross sectional area of a square conduit with that of a circular conduit.

If $R_p$ is the dominant resistance of the measurement circuit, then relative changes in the current I are equal in magnitude to the relative changes in the resistance $|\delta I/I| = |\delta R_p/R_p|$. Consequently, Equations 2 and 3 can both be directly compared to the measured current changes. This comparison is disallowed if $R_p$ is similar in magnitude to other series resistances, such as the electrode/fluid interfacial resistance $R_{e/f}$ or the resistance $R_u$ of the reservoir fluid between the inner electrodes and the conduit. By performing a four-point measurement of the conduit current, this resistance $R_{e/f}$ can be removed from the measurement circuit. $R_u$ can be minimized by placing the voltage sensing electrodes close to the conduit (about 50 μm away on either side) and by designing the reservoir with a cross section much larger than that of the conduit. For a conduit of dimensions 10.5 μm by 1.04 μm², $R_p$ was measured to be 36 MΩ which is in good agreement with the 39 MΩ value predicted by the conduit geometry and the solution resistivity. This confirms that $R_u$ and $R_{e/f}$ have been removed from the circuit.

Solutions of negative charged (carboxyl-coated) latex colloids (Interfacial Dynamics, Inc.) having diameters ranging from 87 to 640 nm were measured. All colloids were suspended in a solution of 5× concentrated Tris-Borate-EDTA (TBE) buffer with a resistivity of 390 Ω cm and pH 8.2. To reduce adhesion of the colloids to the reservoir and conduit walls, 0.05% volume to volume (v/v) of the surfactant Tween 20 was added to each solution. The colloidal suspensions were diluted significantly from stock concentrations to avoid jamming of colloids in the conduit; typical final concentrations were ~$10^8$ particles/ml. The conduit and reservoirs were filled with solution via capillary action.

Suspensions of negatively-charged green fluorescent latex colloids (Interfacial Dynamics, Inc.) of diameters 190 nm, 290 nm, and 370 nm in a 50 mM NaCl solution also have been measured using the device of the invention. Solutions were mixed at number densities of 2.7×$10^{10}$/mL of 190 nm colloids, 1.6×$10^8$/mL of 290 nm colloids, and 7.5×$10^8$/mL of 370 nm colloids. Using fluorescence microscopy, it has been confirmed that the particles responded electrophoretically (moving towards the positive electrodes) in response to an applied voltage.

Figure 7:
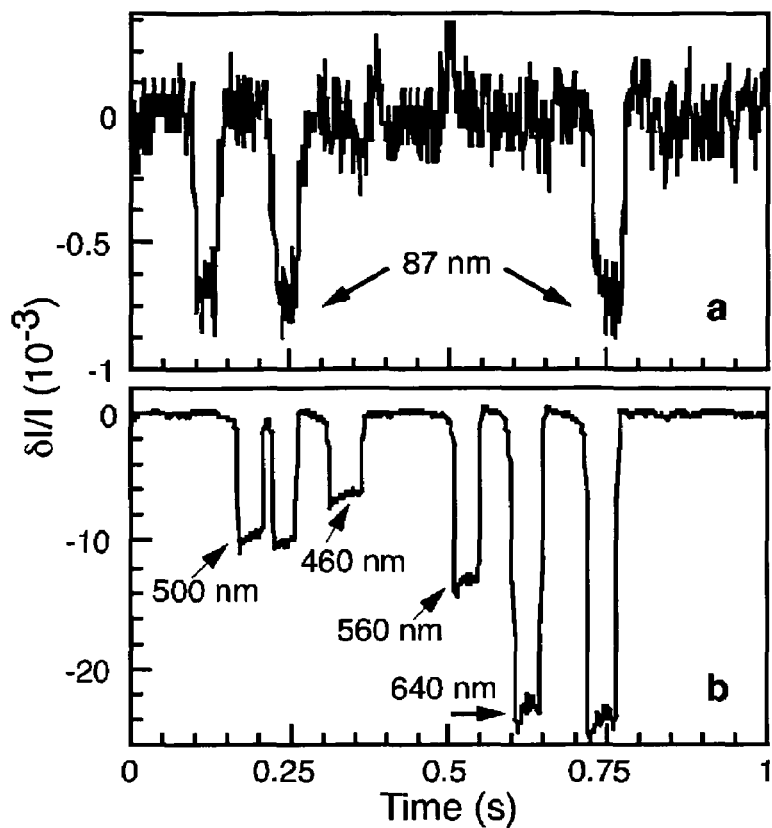
FIG. 7 shows relative changes in baseline current $\delta I/I$ vs time for (a) a monodisperse solution of 87 nm diameter latex colloids measured with an EBL-defined conduit of length 8.3 µm and cross section 0.16 µm$^2$, and (b) a polydisperse solution of latex colloids with diameters 460, 500, 560, and 640 nm measured with a PL-defined conduit of length 9.5 µm and cross section 1.2 µm$^2$. Each downward current pulse represents an individual particle entering the conduit. The four distinct pulse heights in (b) correspond as labeled to the four different colloid diameters.
Figure 13:
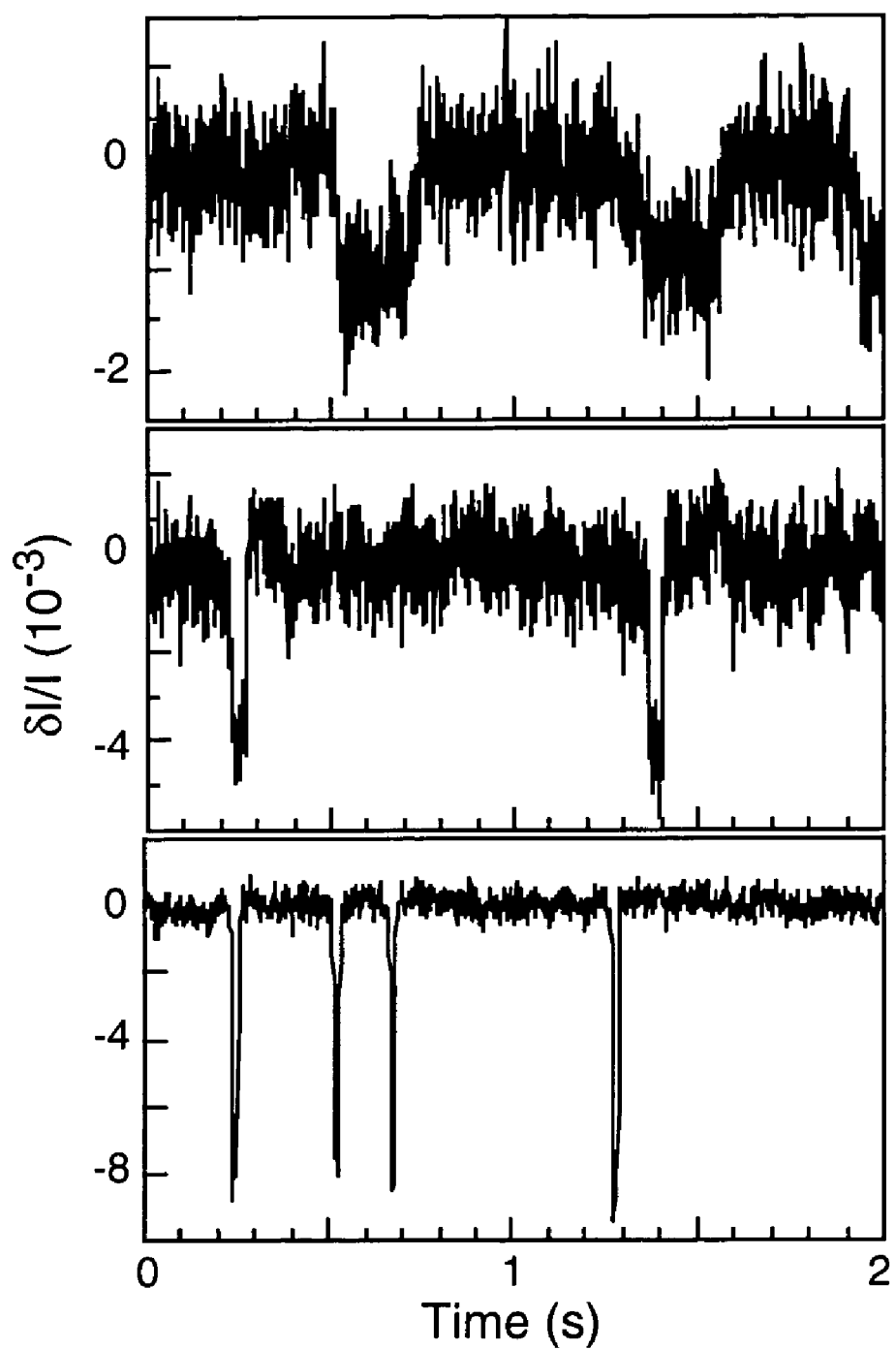
FIG. 13 shows relative changes in baseline current $\delta I/I$ vs time for monodisperse solutions of latex colloids of (a) 190 nm, (b) 290 nm, and (c) 370 nm. Each downward current pulse represents an individual particle entering the conduit.

Representative current traces resulting from measuring solutions of 87, 460, 500, 560, and 640 nm are shown in FIG. 7. Representative current traces resulting from measuring solutions of 190 nm, 290 nm, and 370 nm diameter colloids in FIG. 13. The 87 nm data was obtained using an EBL-defined conduit of length 8.3 μm and cross section 0.16 μm². The 190 nm data was acquired using a conduit of length 4.1 μm and cross section 1.47 by 0.72 μm, while the 370 nm and 290 nm data were acquired with a conduit of length 3.2 μm and cross section 1.33 by 0.75 μm. The data for the latex colloids with diameters 460, 500, 560 and 640 nm was obtained using a PL-defined conduit of length 9.5 μm and cross section 1.2 μm². For the data shown, 0.4 V was applied to the conduit. In other runs, the applied voltage was varied between 0.1 and 1 V to test the electrophoretic response of the colloids. Each downward deflection corresponds to a colloid entering the conduit. It was found that the width of the downward current pulses varied approximately as the inverse of the applied voltage, as is expected for simple electrophoretic motion. The data were sampled at 1 kHz. Absolute current values were typically a few nanoamps, with a noise level of ≤1 pA. The recorded noise primarily originates in the Johnson noise of the conduit.

As previously mentioned, the colloids are driven through the conduit electrophoretically. As the data in FIG. 7 indicate, the transit times in the device ranged from ~100 ms for the 190 nm particles to ~20 ms for the 370 nm particles. For the solutions, the Debye-Hückel length, $1_d$ is much less than the particle diameter. The electrophoretic velocity v of a particle with surface charge density σ in applied electric field E. in a solution of viscosity μ is then $v = \sigma E/\mu 1_d$. The total charge on each colloid $\pi d^2 \sigma$ is expected to be in proportion to the manufacturer-supplied number n of ionizable sulfate groups on each particle. Consequently, the value $v\pi d^2/nE$ should be constant for colloids of different diameter suspended in solutions of the same electrolytic strength. However, this value, calculated from mean transit time for each colloid size, was found to vary over two orders of magnitude for the colloids used. There may be several causes for this deviation. First, there may be remnant electroosmotic flow in the direction opposite the particles motion that is not entirely removed by the surfactant POP6. These effects might vary from run to run. Second, using fluorescence microscopy, events in which colloids momentarily stick to the conduit walls before passing through have been observed. This appears to be reflected in the wide distribution of transit times found in the data. These problems can be alleviated by applying pressure gradients to drive particle flow and/or by suitable choice of surfactant.

Figure 8:
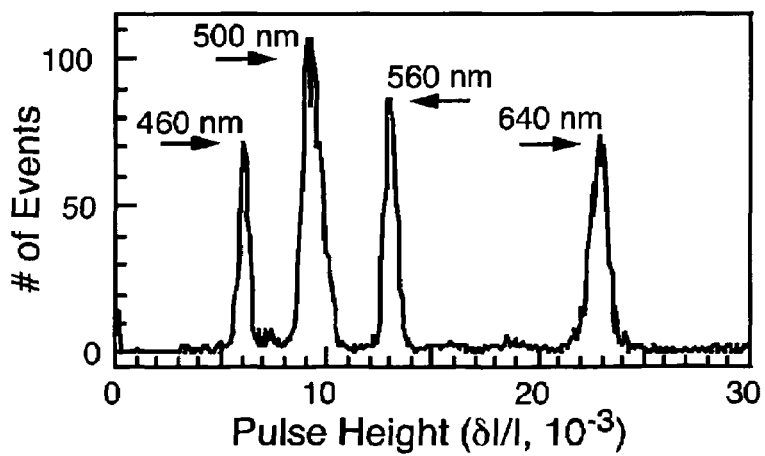
FIG. 8 shows a histogram of pulse heights resulting from measurement of the polydisperse solution described in FIG. 7(b). The resolution for this particular device is ±10 nm in diameter for the particles measured.

FIG. 8 shows a very clear separation between the conduit's response to the differently sized colloids. The peak widths represent the resolution of this device, about ±10 nm in diameter for the measured colloids. This precision approaches the intrinsic variation in colloid diameter of 2-4%, as given by the manufacturer. In this run, the maximum throughput was 3 colloids per second, a rate easily achievable.

Figure 9:
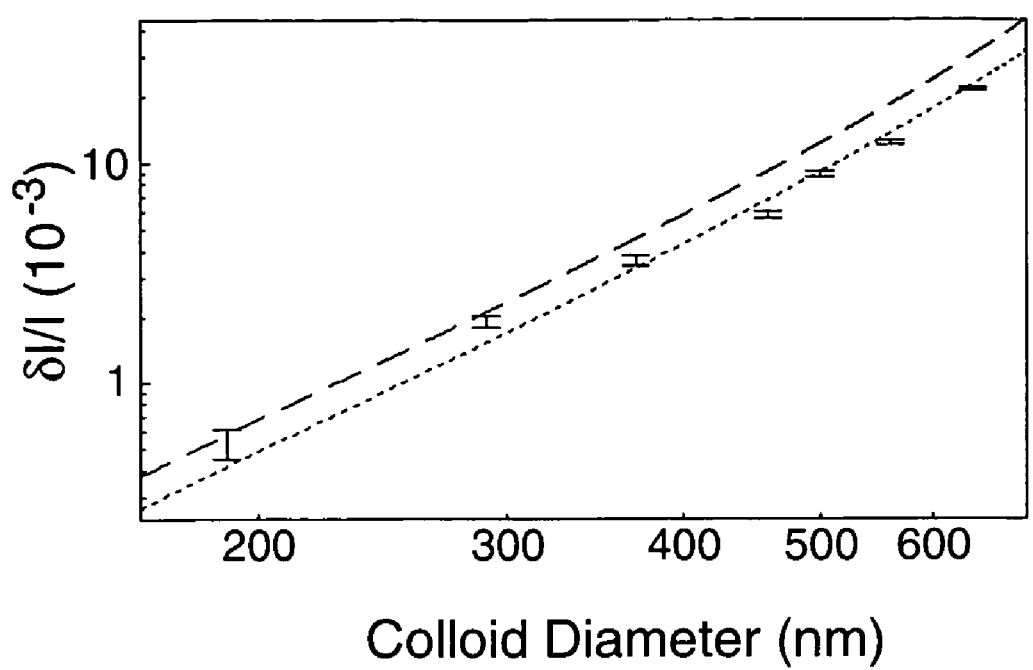
FIG. 9 shows a comparison of measured $\delta I/I$ values (circles) to those predicted by Equation 2 (dotted line) and Equation 3 (dashed line). The measured data were taken over several runs on a single PL-defined conduit of length 10.6 µm and cross section 1.04 µm$^2$. Error bars for the larger colloid sizes are obscured by the size of the plotted point. As the colloid diameter increases, there is a transition from agreement with Equation 3 to Equation 2. This reflects the fact that the derivation of Equation 3 assumes the colloid diameter d is much less than the conduit diameter D; conversely Equation 2 relies on an assumption that holds only as d approaches D, and breaks down for smaller colloids.

FIG. 9 shows the comparison between the mean pulse heights of the current measurements and the values predicted from Equations 2 and 3. The predicted values have been generated using the measured conduit dimensions and the manufacturer-supplied colloid diameters and have been adjusted for uncompensated resistance. Note that D was found by equating the rectangular cross-sectional area of the conduit with the area of a circle. The data is seen to cross over from the small d/D behavior predicted by Equation 3 to the large d/D behavior predicted by Equation 2. As shown, there is excellent agreement between the measured and calculated values, with the measured error insignificant in comparison to the range of pulse heights.

Figure 10:
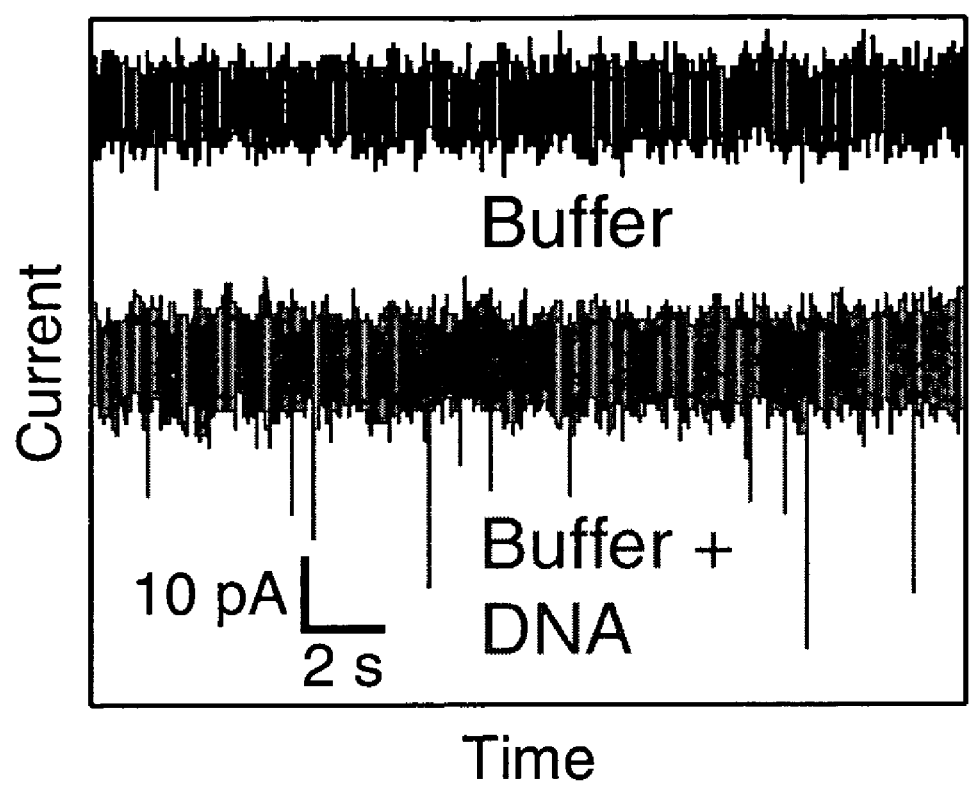
FIG. 10 shows relative changes in baseline current $\delta I/I$ vs time for a solution of bacteriophage λ-DNA. Each downward current pulse represents a single DNA molecule entering the conduit.

The device can be used for characterization of the size and concentration of small particles, including colloids and large biological molecules, in solution. For example, FIG. 10 shows relative changes in baseline current δI/I vs time for a solution of bacteriophage λ-DNA in 0.1 M KCl, 2 mM Tris (pH 8.4) buffer. The upper trace shows the results of analysis of a buffer solution. The lower trace was obtained using a solution of λ-DNA in buffer. Each downward current pulse represents a single DNA entering the conduit. These peaks are absent when measuring only buffer. The data was obtained using a device having a cast cap with a conduit diameter of ~300 nm and a length of ~4 μm.

Previous work on colloids has shown that, for particles of diameter much smaller than that of the conduit, the ratio of peak height to baseline current is approximately equal to the volume ratio of particle to pore:

$$\delta I/I \sim V_{Particle}/V_{pore}$$

The volume of a single lambda DNA can be estimated by approximating it as a cylinder with a 2 nm radium (which includes a 1 nm ionic, or Debye, layer) and a height equal to the contour length of the molecule (~16 μm). Given the known pore volume and a total current I=15 nA, a decrease in current δI~30 pA can be expected when a DNA molecule fully inhabits the conduit. This estimate agrees well with the upper range of measured peak heights and suggests that the measured variation in δI is most likely due to differences in molecular conformation: maximum peak heights arise when an entire molecule inhabits the pore, while smaller peak heights occur when only a portion of a molecule resides within the pore.

By utilizing methods of surface chemistry to attach specific molecules to the device, it can further be used to probe interactions of molecules in solution with those attached to the surface of the device. This can result in measurements of the binding constants between two molecules (such protein-protein, protein-DNA, or enzyme-substrate combinations). In conjunction with other biochemical techniques, these measurements can reveal the nature of the interaction between the two species, which would have implications for the design of drugs.

The device also can be modified so as to be capable of separating and collecting species once those species have passed through the sensor region. In this regard, it will be used for to fractionating large biological molecules such as DNA, RNA, and proteins, and it will also be able to fractionate colloids or particles which are attached to proteins.

The devices can be used to discriminate between conformational states of proteins. This is of great potential use in a very wide range of applications across the biosciences and clinical medicine. In particular, there are a host of potential applications in drug discovery and proteomics. The electronic nature of the devices permits rapid and straightforward storage and reporting of the data obtained.

The microchip Coulter counter described herein can be used as a trigger for further measurements or actions downstream. For example, the change in electrical current or voltage, as a particle passes through the conduit can be used as a trigger for subsequent processes, such as the opening or closing of valves to introduce reagents or diluents; the measurement of other properties of the particle or the liquid medium, such as optical properties of the particle or the pH or capacitance of the fluid; and the like.

In addition, the device can be used as a component of a sorting system. The device is used to detect and monitor the sizes of particles as they pass through the conduit. Particles of a selected size (or range of sizes) can be sent along one flow path (i.e., through a first set of channels) for further processing while particles of other sizes can be sent along a different flow path (i.e., through a second set of channels). Similarly, if an optical detection system is integrated with the device, it is possible to separate particles of a selected size and with a specified fluorescence from those having either a different size and/or a different fluorescence.

Other applications include use in cell-based assays; genomic analysis, such as DNA sizing, quantification, and amplification; protein analysis, crystallization and purification; biochemical assays; integrated biological sample preparation; and single molecule analysis.

Microfluidic or Nanofluidic System

The microchip Coulter counter taught herein can readily be adapted to function with microfluidic or nanofluidic sample delivery systems, requires no environmental support apparatus and can readily be combined with other analytic systems to characterize the biological solutions under study even more completely. See J. M. Cooper, Trends Biotechnol. 17, 226 (1999) and D. C. Duffy, J. C. McDonald, O. J. A. Schueller, and G. M. Whitesides, Anal. Chem. 70, 4974 (1998). These papers are incorporated herein by reference for all purposes. In this specification, microfluidic shall be taken to mean any channel or system wherein the total volume of biological solution at any one time is not more than 10 microliters or wherein the cross-sectional dimensions of the sample container in the measurement region are less than or approximately equal to 100 microns.

Thus, the present invention also provides for an integrated "chip" having microfluidic devices for detecting and measuring molecules or particles. In another embodiment, the chip comprises a plurality of devices for sensing and measuring particles and devices for sorting such identified particles (or molecules), wherein the integrated chip identifies and sorts particles (or molecules) of interest. For example, the integrated chip is capable of sorting a mixture of cells, polynucleotides or proteins, or any other particle or biological molecule of interest.

More specifically, upstream from the Coulter counter may be found one or more of a filtration system, a dilution system, and a means to adjust the driving force of the medium. A gating system for particle analysis or a particle sorter may be included downstream from the device.

More specifically, the device described herein may be used in conjunction with the microfabricated elastomeric valve and pump systems described in published U.S. patent application numbers 20010054778, 20010033796, and 20010029983; U.S. Pat. No. 6,233,048; and PCT publication Nos. WO 01/75176, WO 01/67369, WO 01/32930, and WO 01/01025, each of which is incorporated herein by reference for all purposes.

The devices of the invention also can be integrated with optical detection devices for further analytical applications, and particularly for multiplexed assays or analysis of heterogeneous mixtures. For example, fluorescence of the various particles could be measured as well as size.

Although the foregoing invention has been described in some detail for purposes of clarity of understanding, it will be apparent that certain changes and modifications may be practiced within the scope of the appended claims. Given these possible variations, as well as others more fully described in the detailed specification attached hereto, the described embodiments should be taken as illustrative and not restrictive, and the invention should not be limited to the details given herein but should be defined by the following claims and their full scope of equivalents.

We claim:

1. A device for sensing and characterizing particles by the Coulter principle, said apparatus comprising:
   (a) a conduit that is formed at least in part from poly (dimethylsiloxane), through which a liquid suspension of particles to be sensed and characterized can be made to pass, wherein said conduit has an effective electrical impedance which is changed with the passage of each particle therethrough and wherein the conduit has a cross-sectional area of less than about 1 µm² and a length of less than about 10 µm;
(b) a liquid-handling system for causing said liquid suspension of particles to pass through said conduit; and
(c) a measurement system for sensing the change of electrical impedance in said conduit, wherein the measurement system comprises a four-point electrode system having two inner electrodes and two outer electrodes, wherein the inner electrodes control a voltage applied to the conduit and are positioned external to the conduit, and wherein the outer electrodes inject current into the liquid suspension of particles.

2. The device of claim 1, wherein said liquid-handling system comprises two reservoirs linked by said conduit.

3. The device of claim 2, wherein the surface of the reservoirs has been functionalized to reduce or enhance absorption of the particles to said surface.

4. The device of claim 1, wherein the conduit has a length, in the direction of the passage of the particles, of between about 1 and about 10 micrometers.

5. The device of claim 1, further comprising a microfluidics or nanofluidics system for delivering the liquid suspension of particles to the liquid-handling system.

6. The device of claim 1, wherein the surface of the conduit has been functionalized to reduce or enhance absorption of the particles to said surface.

7. A device for sensing and characterizing particles by the Coulter principle, said apparatus comprising:
(a) a conduit that is formed at least in part from poly (dimethylsiloxane), through which a liquid suspension of particles to be sensed and characterized can be made to pass, wherein said conduit has an effective electrical impedance which is changed with the passage of each particle therethrough and wherein the conduit has a cross-sectional area of less than about 1 µm² and a length, in the direction of the passage of the particles, of between about 0.1 and about 50 micrometers;
(b) a liquid-handling system for causing said liquid suspension of particles to pass through said conduit; and
(c) a measurement system for sensing the change of electrical impedance in said conduit, wherein the measurement system comprises a four-point electrode system having two inner electrodes and two outer electrodes, wherein the inner electrodes control a voltage applied to the conduit and are positioned external to the conduit, and wherein the outer electrodes inject current into the liquid suspension of particles.

8. A device for sensing and characterizing particles by the Coulter principle, said apparatus comprising:
(a) a conduit formed at least in part by an elastomeric material and through which a liquid suspension of particles to be sensed and characterized can be made to pass, wherein said conduit has an effective electrical impedance which is changed with the passage of each particle therethrough and wherein the conduit has a cross-sectional area of between about 1 µm² or less a length, in the direction of the passage of the particles, of between about 1 and about 10 micrometers;
(b) a liquid-handling system for causing said liquid suspension of particles to pass through said conduit; and
(c) a measurement system for sensing the change of electrical impedance in said conduit, wherein the measurement system comprises a four-point electrode system having two inner electrodes and two outer electrodes, wherein the inner electrodes control a voltage applied to the conduit, and are positioned external to the conduit, and wherein the outer electrodes inject current into the liquid suspension of particles.

9. The device of claim 8, wherein said liquid-handling system comprises two reservoirs linked by said conduit.

10. The device of claim 9, wherein the surface of the reservoirs has been functionalized to reduce or enhance adsorption of the particles to said surface.

11. The device of claim 8, further comprising a microfluidics or nanofluidics system for delivering the liquid suspension of particles to the liquid handling system.

12. The device of claim 8, wherein the surface of the conduit has been functionalized to reduce or enhance adsorption of the particles to said surface.

13. The device of claim 8, wherein the elastomeric material comprises polyisoprene, polybutadiene, polychloroprene, polyisobutylene, poly(styrene-butadiene-styrene), polyurethane, poly(dimethylsiloxane) or silicone.

14. The device in claim 8, wherein the device is substantially transparent.

15. The device of claim 14, wherein the device further comprises an optical detection system.

16. A method for sensing and characterizing particles by the Coulter principle, said method comprising:
(a) passing a liquid suspension of particles to be sensed and characterized through a conduit formed at least in part by an elastomeric material, wherein said conduit has an effective electrical impedance which is changed with the passage of each particle therethrough and wherein the conduit has a cross-sectional area of less than about 1 µm² and a length, in the direction of the passage of the particles, of between about 1 and about 10 micrometers; and
(b) monitoring electrical current through or voltage across, said conduit with a four-point electrode system having two inner electrodes and two outer electrodes, wherein the inner electrodes control a voltage applied to the conduit, and are positioned external to the conduit, to sense the approach of particles to, the presence and characteristics of particles passing through, or the departure of particles from, said conduit, and wherein the outer electrodes inject current into the liquid suspension of particles.

17. The method of claim 16, wherein the particle's residence time in the conduit is also measured.

18. The method of claim 16, further comprising a microfluidics or nanofluidics system for delivering the liquid suspension of particles to the conduit.

19. The method of claim 16, wherein the elastomeric material comprises polyisoprene, polybutadiene, polychloroprene, polyisobutylene, poly(styrene-butadiene-styrene), polyurethane, poly(dimethylsiloxane), or silicone.

20. The method of claim 16, wherein the sensing of the approach of particles to, the presence and characteristics of particles passing through, or the departure of particles from, said conduit, initiates additional measurements or actions on said particles.

21. A method for sensing and characterizing particles by the Coulter principle, said method comprising:
(a) passing a liquid suspension of particles to be sensed and characterized through a conduit formed at least in part by an elastomeric material, wherein said conduit has an effective electrical impedance which is changed with the passage of each particle therethrough and wherein the conduit has a cross-sectional area of less than about 1 µm² and a length of less than about 50 µm; and (b) monitoring electrical current through or voltage across, said conduit with a four-point electrode system having two inner electrodes and two outer electrodes, wherein the inner electrodes control a voltage applied to the conduit, and are positioned external to the conduit, to sense the approach of particles to, the presence and characteristics of particles passing through, or the departure of particles from, said conduit, and wherein the outer electrodes inject current into the liquid suspension of particles.

22. The method of claim 21, wherein the particle's residence time in the conduit is also measured.

23. The method of claim 21, further comprising a microfluidics or nanofluidics system for delivering the liquid suspension of particles to the conduit.

24. The method of claim 21, wherein the elastomeric material comprises polyisoprene, polybutadiene, polychloroprene, polyisobutylene, poly(styrene-butadiene-styrene), polyurethane, poly(dimethylsiloxane), or silicone.

25. The method of claim 21, wherein the conduit is substantially transparent.

26. The method of claim 25, further comprising the step of optically detecting the particles as the particles pass through said conduit.

27. The method of claim 21, wherein the sensing of the approach of particles to, the presence and characteristics of particles passing through, or the departure of particles from, said conduit, initiates additional measurements or actions on said particles.

* * * * *